United States Patent [19]

Hirata et al.

[11] Patent Number: 4,734,494
[45] Date of Patent: Mar. 29, 1988

[54] OPTICALLY ACTIVE 3-HALO CARBACEPHEMS

[75] Inventors: Tadashi Hirata, Yokohama; Yukio Hashimoto, Yamato; Ikuo Matsukuma, Yokkaichi; Shigeo Yoshiie, Sakai; Seigo Takasawa, Hadano, all of Japan

[73] Assignee: Kyowa Hakko Kogyo Co., Ltd., Tokyo, Japan

[21] Appl. No.: 926,889

[22] Filed: Nov. 6, 1986

Related U.S. Application Data

[60] Continuation of Ser. No. 825,696, Feb. 3, 1986, abandoned, which is a continuation of Ser. No. 732,893, May 9, 1985, abandoned, which is a continuation of Ser. No. 643,101, Aug. 22, 1984, abandoned, which is a continuation of Ser. No. 518,315, Jul. 29, 1983, abandoned, which is a continuation of Ser. No. 291,129, Aug. 7, 1981, abandoned, which is a division of Ser. No. 206,639, Nov. 13, 1980, Pat. No. 4,302,541.

[30] Foreign Application Priority Data

Nov. 14, 1979 [JP] Japan ................... 54-146488

[51] Int. Cl.$^4$ .................. C07D 487/04; C12P 17/18; C07B 19/02
[52] U.S. Cl. ................................................. 540/205
[58] Field of Search .......................................... 540/205

[56] References Cited

U.S. PATENT DOCUMENTS 4,123,528  10/1978  Cama ........................... 540/205

FOREIGN PATENT DOCUMENTS

| 0014475 | 8/1980 | European Pat. Off. |
| 0014476 | 8/1980 | European Pat. Off. |
| 2355209 | 5/1974 | Fed. Rep. of Germany |
| 2714880 | 10/1978 | Fed. Rep. of Germany |
| 2716707 | 10/1978 | Fed. Rep. of Germany |
| 2911786 | 9/1979 | Fed. Rep. of Germany |
| 2911787 | 9/1979 | Fed. Rep. of Germany |
| 2342974 | 9/1977 | France |
| 1455016 | 11/1976 | United Kingdom |
| 2017102 | 10/1979 | United Kingdom |
| 2017103 | 10/1979 | United Kingdom |

OTHER PUBLICATIONS

Hirata et al., Chem. Abs., 93, 239247t.
Uyeo et al., Chem. Pharm. Bull., 28, 1563–77, (1980).
J. American Chem. Soc., 96, 7584:5, (1974).

*Primary Examiner*—Mark L. Berch
*Attorney, Agent, or Firm*—Fitzpatrick, Cella, Harper & Scinto

[57] ABSTRACT

Optically active cephalosporin analogs are produced by optically selective deacylation of an optically inactive acylated analog. The compounds are useful as intermediates in the preparation of optically active acylated antimicrobial agents.

3 Claims, No Drawings

OPTICALLY ACTIVE 3-HALO CARBACEPHEMS

This application is a continuation of application Ser. No. 825,696, filed Feb. 3, 1986, now abandoned, which is a continuation of application Ser. No. 732,893, filed May 9, 1985, now abandoned, which is a continuation of application Ser. No. 643,101, filed Aug. 22, 1984, now abandoned, which is a continuation of application Ser. No. 518,315, filed July 29, 1983, now abandoned, which is a continuation of application Ser. No. 291,129, filed Aug. 7, 1981, now abandoned, which is a division of application Ser. No. 206,639 filed Nov. 13, 1980, now U.S. Pat. No. 4,302,541.

The present inventors have succeeded in preparing carbacephem compounds having various substituents at the 4-, 5- and 3-positions [The numbering system is as shown in the general formula (I)]. The compounds are described in the specification of Japanese Patent Application (referred to as "JPA", hereinafter) Nos. 34696/78 [Japanese Published Unexamined Patent Application (referred to as "JPUPA", hereinafter) No. 128591/79] [German Offenlegungsschrift (referred to as "G.O." hereinafter) 2911786], 122403/78 (JPUPA No. 49376/80), 133072/78 (JPUPA No. 59186/80), 162005/78 (JPUPA /No. 87788/80) and 8408/79 (JPUPA No. 100384/80), and U.S. patent application Ser. No. 23645.

Further, the present inventors have succeeded in preparing novel acylated carbacephems which are new antibiotics having strong antibacterial activites. These are described in JPA Nos. 34696/78 (JPUPA No. 128591/79), 122402/78 (JPUPA No. 49375/80), 127027/78 (JPUPA No. 53290/80), 133071/78 (JPUPA No. 59185/80), 162006/78 (JPUPA No. 87789/80), 162007/78 (JPUPA No. 87790/80), 162008/78 (JPUPA No. 87791/80), 8409/79 (JPUPA No. 100391/80), 92035/79 and 116720/79, G.O. 2911787, and U.S. patent application Ser. No. 23646.

However, cephalosporin analogs mentioned above are prepared by synthetic methods using optically inactive staring compounds, and they are optically inactive dl [represented by (±)] compounds unless they have optically active acyl group. More specifically, compounds represented by the general formula (I) wherein the hydrogen atoms at the 6- and 7-positions have cis configuration are present as a mixture of equal amounts of the mirror image compounds represented by the formulae (I-1) and (I-2)

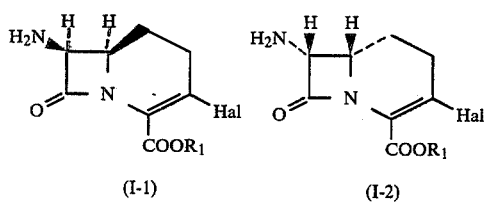

herein $R_1$ and Hal have the same significance as defined above.

The compounds represented by the general formula (IV)

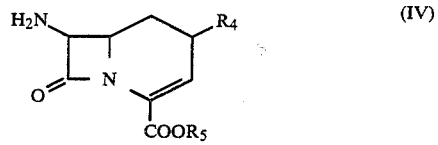

(wherein $R_4$ represents a hydrogen, a lower alkyl group or a lower acyl group and $R_5$ represents a hydrogen or a protective group of carboxylic acid) described in JPUPA No. 128591/79 was also present as a mixture of equal amounts of the mirror image compounds represented by the general formulae (IV-1) and (IV-2)

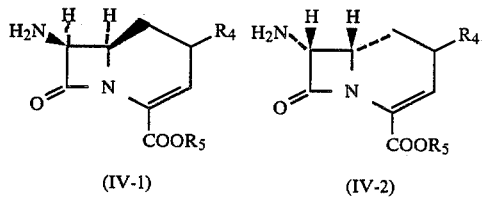

wherein $R_4$ and $R_5$ have the same significance as defined above.

The present inventors have disclosed optically active compound of the compound represented by the general formula (IV) and method of producing the same in Japanese Patent Application No. 14533/79 (JPUPA No. 18872/80) wherein the optically active compound is defined as the compound represented by the general formula (IV-1).

The present inventors have succeeded in isolating and preparing one of the optically active mirror image compounds of the compound represented by the general formula (I) and completed the present invention. That is, the present inventors have first succeeded in preparing optically active compounds of cephalosporin analogs represented by the general formula (I) by optically selective deacylation reaction using an enzyme and an optically inactive dl compound having an acyl group as a starting compound. The desired compound is obtained in a remarkably high yield by the method.

SUMMARY OF THE INVENTION

The optically active compounds of cephalosporin analogs represented by the formula (I), that is, the compound represented by the assumed absolute structural formula (I-1) and salts thereof are prepared in the present invention.

In the foregoing general formula (I), the ester group $COOR_1$ is a group readily convertible in COOH employed in the chemistry of penicillins and cephalosporins.

The group $R_1$, may be a straight-chain or branched alkyl group having 1 to 5 carbon atoms such as methyl, ethyl, n-propyl, i-propyl, n-butyl, i-butyl, sec-butyl, t-butyl, and the like; a straight-chain or branched alkoxymethyl group having 1 to 5 carbon atoms such as methoxymethyl, ethoxymethyl, and the like; a straight-chain or branched halogenated alkyl group having 1 to 5 carbon atoms such as chloromethyl, 2,2,2-trichloroethyl, 2,2,2-trifluoroethyl, and the like; a lower alkylsulfonylethyl group such as methylsulfonylethyl, ethylsulfonylethyl, and the like; an arylmethyl group having 7 to 12 carbon atoms such as benzyl, diphenylmethyl, trityl, triphenylmethyl, and the like; a substituted arylmethyl group having 7 to 20 carbon atoms wherein the substituent is methoxy group, nitro group, or the like and the number of the substituents on the phenyl ring is 1 to 5; or a protective group of carboxylic acid represented by the general formula (II)

wherein $R_2$ represents a straight-chain or branched lower alkyl group having 1 to 5 carbon atoms, a straight-chain or branched lower alkoxy group having 1 to 5 carbon atoms, or a phenyl group, and $R_3$ represents a hydrogen or a straight-chain or branched lower alkyl group having 1 to 5 carbon atoms. As the halogen atom, chlorine, bromine or iodine is exemplified.

The optically active compounds of cephalosporin analogs represented by the general formula (I), that is, one of the enantiomers, are prepared, according to the present invention, by an optically selective deacylation reaction using an enzyme and an optically inactive dl compound having an acyl group as a certain starting compound. The desired compound is obtained in a remarkably high yield by this method.

The optically active compounds obtained in the present invention are assumed to have the absolute structure represented by the general formula (I-1), that is (6R, 7S), from various properties, stronger antimicrobial activity of their acyl derivatives as compared with the corresponding optically inactive dl-compound and the relationship between the absolute chemical structure of cephalosporins and activities thereof. These compounds are particularly useful as intermediates in the preparation of optically active acylated compounds which are strong antibacterial agents.

In the following description, the optically active compounds are described with reference to the general formula (I-1). Additionally, the compounds in the following examples and reference examples are named according to the assumed absolute structural formula.

DETAILED DESCRIPTION OF THE INVENTION

Optically active compounds of the cephalosporin analogs represented by the general formula (I) or compounds represented by the assumed absolute structural formula (I-1) are produced by optically selective deacylation of a compound represented by the general formula (III)

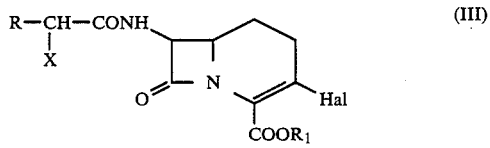

wherein R represents a substituted or unsubstituted, saturated or unsaturated six-membered carbocyclic or five-membered heterocyclic group, X represents a hydrogen, an amino group, a hydroxy group or a lower alkyl group, $R_1$ and Hal have the same significance as defined above, and the hydrogens at the 6- and 7-positions have cis configuration.

As the unsaturated six-membered carbocyclic and five-membered heterocyclic group, phenyl group, cyclohexenyl group, cyclohexadienyl group, thienyl group and furyl group are exemplified. As the substituent of the carbocyclic and the heterocyclic group, hydroxy group, halogens, nitro group, methansulfonamide group, and the like are mentioned. As the lower alkyl group, a straight-chain or branched alkyl groups having 1 to 5 carbon atoms such as methyl, ethyl, n-propyl, i-propyl, n-butyl, i-butyl, sec-butyl, and the like are mentioned.

The optically selective deacylation of Compound [III] to obtain optically active Compound [I-1] is carried out in the presence of an enzyme obtained from a microorganism capable of producing optically active Compound [I-1] by optically selective deacylation of Compound [III].

As the microorganism having an ability of optically selective deacylation, microorganisms belonging to the genus Aeromonas, Achromobacter, Arthrobacter, Acetobacter, Alcaligenes, Escherichia, Xanthomonas, Kluyvera, Gluconobacter, Clostridium, Comamonas, Corynebacterium, Sarcina, Staphylococcus, Spirillum, Bacillus, Pseudomonas, Flavobacterium, Brevibacterium, Protaminobacter, Proteus, Beneckea, Micrococcus, Mycoplana or Rhodopseudomonas are used. The following strains are examples of the microorganism.

| | |
|---|---|
| Aeromonas hydrophila | IFO 12634 |
| Achromobacter aceris | IFO 3320 |
| Arthrobacter simplex | ATCC 15799 |
| Acetobacter aurantius | IFO 3245 |
| Acetobacter sp. | ATCC 21760 |
| Alcaligenes faecalis | ATCC 8750 |
| Escherichia coli | ATCC 11105 |
| Escherichia coli | ATCC 13281 |
| Xanthomonas citri | IFO 3835 |
| Xanthomonas physalidicola | IFO 13555 |
| Kluyvera citrophila | ATCC 21285 |
| Gluconobacter liquefaciens | ATCC 14835 |
| Gluconobacter dioxyacetonicus | IFO 3271 |
| Clostridium acetobutylicum | ATCC 824 |
| Comamonas terrigena | IFO 12685 |
| Corynebacterium tritici | IFO 12164 |
| Sarcina lutea | ATCC 9341 |
| Staphylococcus aureus | IFO 3060 |
| Spirillum methamorphum | IFO 12012 |
| Bacillus megaterium | ATCC 14945 |
| Pseudomonas aeruginosa | IFO 3451 |
| Pseudomonas melanogenum | ATCC 17808 |
| Flavobacterium sp. | ATCC 21429 |
| Brevibacterium cerinum | ATCC 15112 |
| Protaminobacter alboflavus | IFO 13221 |
| Proteus rettgeri | ATCC 9250 |
| Beneckea hyperoptica | ATCC 15803 |
| Micrococcus luteus | AHU 1427 |
| Mycoplana bullata | IFO 13267 |
| Mycoplana dimorpha | IFO 13213 |
| Rhodopseudomonas spheroides | ATCC 21286 |

For carrying out the optically selective deacylation reaction, the enzyme may be provided, more specifically, in any of the following forms:
1. As the culture liquor of the microorganism or treated matter thereof;
2. As cell bodies recovered from the culture broth by centrifugation which may be washed with saline water (usually about 1%), buffer solution and the like, or as a cell suspension;
3. As a disrupted cell suspension, i.e., a suspension of the cell bodies disrupted mechanically or chemically;
4. As a cell free extract, i.e., a liquid obtained by removing the disrupted cell bodies from the disrupted cell suspension; or
5. As a purified enzyme solution which is obtained by recovering the enzyme protein with ammonium sulfate from the cell free extract and subjecting the enzyme protein to gel filtration, ion-exchange cellulose column chromatography, ion-exchange Sephadex column chromatography, and the like.

Cells or the purified enzyme immobilized by a conventional method may be used.

The reaction is carried out at a temperature of 0° to 40° C., preferably 15° to 35° C. and at a pH of 5 to 8 in an inactive solvent which does not affect the reaction.

As the solvent, water is most preferably used. In order to dissolve the substrate or cephalosporin analogs, organic solvents such as acetone, methane, ethanol, N,N-dimethylformamide, dimethylsulfoxide, and the like may be used. It is effective to add phosphate buffer, Veronal buffer or citric acid buffer to control the pH in the reaction. Reaction time, which is varied according to the kind and concentration of enzymes, the kind and concentration of substrates, reaction temperature or reaction pH, is generally 30 minutes to 24 hours. It is most preferable to terminate the reaction when the reaction ratio reaches maximum.

The concentration of cells is preferably 1 to 50 mg by dry weight per 1 ml of the reaction solutions. When a purified enzyme is used, it is appropriate to use the amount of the enzyme having the same activity as that of the dry cell. The substrate Compound [III] is used in an amount of 0.5 to 50 mg per 1 ml of the reaction solution.

In the event the microorganism utilized also produces an enzyme such as β-lactamase, esterase or the like, which tends to prevent the desired reaction, such microorganisms can be mutated by known techniques to obtain a mutant strain which has a reduced productivity of the undesirable enzyme. Alternatively, inhibitors of such enzymes may be added in the reaction system to raise the reaction ratio.

After the completion of the reaction, isolation of the desired compound is carried out by a conventional method employed in the isolation and purification of organic compounds from culture liquors such as absorption using various carriers, ion-exchange chromatography, gel filtration, liquid-liquid extraction, and the like.

Among the compounds represented by the general formula (I), the optically active compounds of the cephalosporin analogs represented by the general formula (I-3)

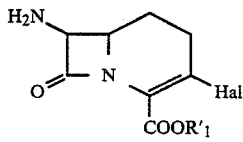
(I-3)

(wherein Hal has the same significance as defined above, $R'_1$ represents a protective group of carboxylic acid and the hydrogens at the 6- and 7-positions have cis configuration) may also be obtained by the esterification of the optically active cephalosporin analogs represented by the general formula (I-4)

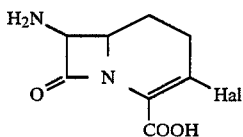
(I-4)

(wherein Hal has the same significance as defined above, and the hydrogens at the 6- and 7-positions have cis configuration) by a conventional method.

Starting compounds of the present invention, Compounds [III] are prepared by introducing an acyl group represented by the general formula (VI)

(VI)

wherein R' represents a substituted or unsubstituted unsaturated six-membered carbocyclic or five-membered heterocyclic group wherein the substituent represents a hydroxy group, a substituted hydroxy group, a halogen atom, a nitro group or a methanesulfonamide group, and X' represents a hydrogen, an amino group, a substituted amino group, a hydroxy group, a substituted hydroxy group or a lower alkyl group to the optically inactive compound represented by the general formula (I) and, if necessary, eliminating the protective group or substituents of hydroxy group, amino group and the like.

Method of producing optically inactive Compound (I) is described in detail in JPA No. 92035/79. An example of the method is described in Reference Example below.

The present optically active compounds, Compound [I-1], themselves are expected to have antibacterial activities and acylated compounds of the optically active Compound [I-1] have much stronger antimicrobial activities than the acyl compounds of the corresponding enantiomeric Compound [I-2]. Examples of such compounds and antimicrobial activities thereof are described in Reference Examples.

The present invention is explained by the following Example.

EXAMPLE 1

Preparation of (6R, 7S) 7-amino-3-chloro-1-azabicyclo[4,2,0]oct-2-en-8-on-2-carboxylic acid 1-1. Preparation of cell suspension (1) Cultivation of a microorganism having an ability of optically selective deacylation As the seed strain, *Kluyvera citrophila* ATCC 21285 [Biological properties are described in J. General Applied Microbiology 3, 28–31 (1957)] is used.

As the seed medium, an aqueous solution containing 1% polypepton, 1% yeast extract, 0.5% meat extract, 0.5% sodium glutamate and 0.25% sodium chloride and adjusted to a pH of 7.0 with 5N-NaOH is used. One loopful of the seed strain is inoculated into 10 ml of the seed medium in a 50 ml-large test tube and culturing is carried out at a temperature of 30° C. for 24 hours. The whole of the seed broth is inoculated into 300 ml of the culture medium in a 2 l-Erlenmeyer flask and culturing is carried out at a temperature of 30° C. with shaking. The composition of the main culture medium is the same as that of the seed medium.

(2) Preparation of cell suspension

After culturing for 24 hours, the culture broth is subjected to centrifugation to obtain cell bodies. The cells are washed twice with 50 ml of 0.9% saline solution and suspended in a concentration of 40 mg/ml by dry weight in 1/30M phosphate buffer solution (pH 8.0).

1-2. Preparation of substrate solution

In this step, 200 mg of (±)-cis-7-phenylacetamido-3-chloro-1-azabicyclo[4,2,0]cis-2-en-8-on-2-carboxylic acid obtained as in Reference Example 1 below is added into 9 ml of 1/30M phosphate buffer (pH 8.0). Since the compound is not dissolved, 2N-NaOH is added in a small portion and the mixture is again adjusted to a pH of 8.0 to dissolve the compound. Finally, deionized water is added to make 10 ml of a solution.

1-3. Enzyme reaction

In this step, 10 ml of the cell suspension mentioned above is added to 10 ml of the substrate solution and enzyme reaction is carried out at a temperature of 40° C. for 80 minutes. Time course of the reaction is illustrated in Table 1.

TABLE 1

| Reaction period (minutes) | The amount of Compound [I-1] produced (mg/ml) | Yield (Mol ratio, %) |
| --- | --- | --- |
| 10 | 1.3 | 20 |
| 20 | 1.8 | 28 |
| 40 | 2.0 | 31 |
| 60 | 2.3 | 36 |
| 80 | 2.4 | 37 |

1-4. Isolation and Purification of the desired compound

After the completion of the reaction, cells are removed by centrifugation from the reaction solution. The supernatant is concentrated under reduced pressure to make 5 ml of solution. The solution is charged on a column (diameter: 1.75 cm, height: 42 cm) packed with Diaion HP-10 (product of Mitsubishi Kasei Kogyo Co., Ltd.). Elution is carried out with deionized water. The desired compound is eluted from 90 ml to 120 ml of the fractions. The fractions are concentrated under reduced pressure, to make 2 ml of solution and the solution is adjusted to pH 3.5 with 1N-hydrochloric acid to deposit crystals. The crystals are recovered by filtration, washed with a small amount of methanol and dried to obtain 38 mg of a white powder. Properties of the product are as follows.

IR(KBr)$\nu_{max}^{cm-1}$: 3200, 1800, 1790(sh), 1775(sh), 1640(sh), 1630, 1555.

NMR(100M D$_2$O-DSS)δ: 4.47(1H, d, J=5.1 Hz), 3.88(1H, m), 2.64(2H, m), 1.93(2H, m).

Optical rotation $[\alpha]_D^{25°} = -2.7°$ (c=0.24, 1M phosphate buffer pH 7.0).

REFERENCE EXAMPLE 1

Preparation of (±)-cis-7-phenylacetamido-3-chloro-1-azabicyclo[4,2,-0]oct-2-en-8-on-2-carboxylic acid

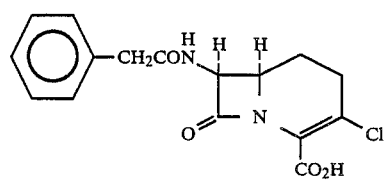

In this Example, 150 mg (0.45 m mole) of the trifluoroacetate of (±)-cis-7-amino-3-chloro-1-azabicyclo-[4,2,0]oct-2-en-8-on-2-carboxylic acid prepared as in the method described in JPUPA No. 87791/80 is dissolved in a mixture of 2 ml of water and 2 ml of acetone and 134 mg (1.5 m mole) of sodium bicarbonate is added to the solution to make the solution homogeneous. To the mixture is added 84.2 mg (0.54 mole) of phenylacetylchloride dissolved in 0.5 ml of acetone under cooling in one hour and the mixture is stirred for 3 hours. The reaction mixture is added to a pH of 2 with 1N hydrochloric acid and extracted 5 times with 2 ml of ethyl acetate. The extract is concentrated under reduced pressure and dried to obtain 80 mg (55.0%) of the desired compound.

IR$\nu_{max}^{KBr}$ (cm$^{-1}$): 1790, 1705, 1630, 1560.

NMR (CD$_3$OD)δ: 7.29(5H, s), 5.36(1H, d, J=5 Hz), 3.79–3.99(1H, m), 2.56–2.75(2H, m), 1.17–2.02(2H, m).

REFERENCE EXAMPLE 2

Preparation of (6R, 7S) 7-(R)-2-phenylglycinamido-3-chloro-1-azabicyclo[4,2,-0]oct-2-en-8-on-2-carboxylic acid

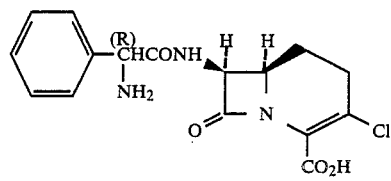

2-1. Preparation of cell suspension (a) Cultivation of a microorganism having an ability of optically selective acylation As a seed strain, *Pseudomonas melanogenum* ATCC 17808 [Biological properties are described in Journal of the Agricultural Chemical Society of Japan, 37, 71 (1963)] is used.

As a seed medium, an aqueous solution containing 1% polypepton, 1% yeast extract, 0.5% meat extract, 0.5% sodium glutamate and 0.25% sodium chloride and adjusted to a pH of 7.0 with 5N-NaOH is used. One loopful of the seed strain is inoculated into 10 ml the seed medium in a 50 ml-large test tube and culturing is carried out at a temperature of 30° C. for 24 hours. The whole amount of the seed medium is put into 300 ml of the culture medium in a 2 l-Erlenmeyer flask and culturing is carried out with shaking at a temperature of 30° C. The composition of the culture medium is the same as that of the seed medium.

(b) Preparation of cell suspension

After culturing for 24 hours, cell bodies are recovered from the culture broth by centrifugation and washed 2 times with 50 ml of 0.9% saline solution. The concentrate is charged on a column (diameter: 1.6 cm, height: 64.5 cm) packed with 130 ml of Sephadex-LH20 (product of Pharmacia Fine Chemicals Inc.) and elution is carried out with a mixture of water and methanol (50:50). The desired compound is eluted in 55 ml to 75 ml of fractions. The fractions are concentrated under reduced pressure and the residue is lyophilized to obtain 12.8 mg of a white powder. The cells are suspended in a concentration of 20 mg/ml by dry weight in 1/30M phosphate buffer (pH 6.5).

2-2. Preparation of substrate solution 100 mg of (6R, 7S) 7-amino-3-chloro-1-azabicyclo[4,2,0]oct-2-en-8-on-2-carboxylic acid [starting compound (a)] obtained as in Example 1 and 800 mg of the hydrochloride of D-phenylglycine methylester are added to 9 ml of 1/30M potassium phosphate buffer (pH 6.5). 5N-KOH is added in small portions and the mixture is again adjusted to a pH of 6.5 to dissolve two starting compounds. Finally, deionized water is added to make 10 ml of a solution.

2-3. Enzyme reaction

In this step, 10 ml of the cell suspension is added to 10 ml of the substrate solution and enzyme reaction is carried out at temperature of 30° C. for 1.5 hours. The reaction is monitored by high speed liquid chromatography using TRI ROTAR and Prepack column Nucleosil $10C_{18}$. Elution is carried out with 7% methanol-0.2M $KH_2PO_4$ solution. Reaction reaches maximum in 1.5 hours. Yield to the starting compound (a) is 90%.

2-4. Isolation and purification of the desired compound

After the completion of reaction, cell bodies are removed from the reaction solution by centrifugation. The supernatant is concentrated under reduced pressure and charged on a colum (diameter: 1.6 cm, height: 50 cm) packed with 100 ml of Diaion HP-10. After adding 200 ml of deionized water, elution is carried out with 25% aqueous methanol solution. The fractions containing the desired compound are concentrated under reduced pressure to make 5 ml of a concentrate. The concentrate is charged on a column (diameter: 1.6 cm, height: 64.5 cm) packed with 130 ml of Sephadex LH 20 and elution is carried out with a mixture of water and methanol (50:50). The desired compound is eluted in 55 ml to 75 ml of fractions. The fractions are concentrated under reduced pressure and lyophilized to obtain 128 mg of a white powder. Properties of the product are as follows.

$[\alpha]_D^{21°} = +34.0°$ (c=0.35, $H_2O$).

Melting point: 300° C. or more (browning).

IR (KBr)$\nu_{max}^{cm-1}$: 1770, 1700, 1620.

NMR($D_2O$)$\delta$(ppm): 7.51(5H, s), 5.36(1H, d, J=4.6 Hz), 5.19(1H, s), 3.83–4.00(1H, m), 2.41–2.56(2H, m), 1.49–1.76(1H, m), 1.14–1.45(1H, m).

Antibacterial activities of the compound obtained in Reference Example 2 are shown in the following table. Heart Infusion Agar Dilution Method (pH 7.2) is used. Cefazolin and cephalexin are used as a control.

| Microorganism | Cefazolin | Cephalexin | The compound obtained in Reference Example 2 |
|---|---|---|---|
| Staphlococcus aureus 209-P | ≦0.05 | 0.2 | 0.1 |
| Staphylococcus aureus Smith | 0.4 | 3.12 | 1.56 |
| Staphylococcus epidermidis | 0.78 | 3.12 | 1.56 |
| Escherichia coli NIHJC-2 | 1.56 | 12.5 | 1.56 |
| Escherichia coli Juhl | 1.56 | 12.5 | 1.56 |
| Klebsiella pneumoniae 8045 | 0.78 | 3.12 | 0.2 |
| Klebsilella pneumoniae Y-60 | 3.12 | 50 | 6.25 |
| Serratia marcescens T-26 | >100 | — | >100 |
| Serratia marcescens T-55 | 50 | 50 | 6.25 |
| Proteus mirabilis 1287 | 12.5 | 25 | 3.12 |

I claim:

1. Optically active (6R, 7S) compounds represented by the formula:

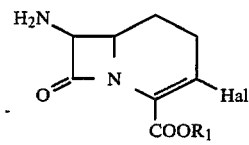

wherein $R_1$ represents hydrogen or a carboxyl-protecting group selected from the group consisting of: straight-chain or branched alkyl having 1 to 5 carbons, straight-chain or branched alkoxymethyl having 1 to 5 carbons, straight-chain or branched halogenated alkyl having 1 to 5 carbons, lower alkylsulfonylethyl, arylmethyl having 7 to 12 carbons, substituted arylmethyl having 7 to 20 carbons wherein the substituent is methoxy or nitro and the number of substituents on the phenyl ring is 1 to 5, and a protective group of carboxylic acid represented by the formula:

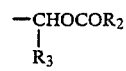

wherein $R_2$ is straight-chain or branched lower alkyl having 1 to 5 carbons, straight-chain or branched lower alkoxy having 1 to 5 carbons, or phenyl; and $R_3$ is hydrogen or straight-chain or branched lower alkyl having 1 to 5 carbons;

Hal represents a halogen atom; and pharmaceutically acceptable salts thereof.

2. The compound according to claim 1, wherein $R_1$ is a hydrogen.

3. The compound according to claim 2, wherein Hal is a chlorine atom, that is (6R, 7S) 7-amino-3-chloro-1-azabicyclo[4,2,0]oct-2-en-8-on-2-carboxylic acid.

* * * * *

UNITED STATES PATENT AND TRADEMARK OFFICE
CERTIFICATE OF CORRECTION

PATENT NO. : 4,734,494
DATED : March 29, 1988
INVENTOR(S) : TADASHI HIRATA, ET AL.

It is certified that error appears in the above-identified patent and that said Letters Patent is hereby corrected as shown below:

Column 1, line 15, insert entire page 1 of Specification as follows:

--Background of the Invention

The present invention relates to optically active cephalosporin analogs and, more particularly, it pertains to optically active compounds of cephalosporin analogs represented by the general formula (I)

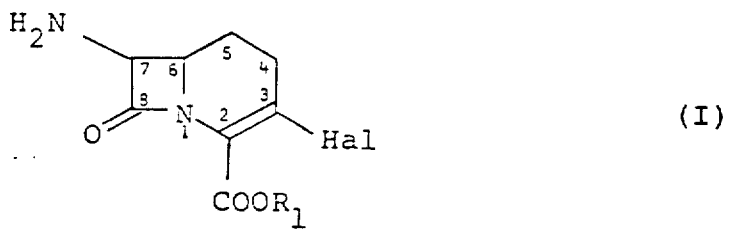

wherein $R_1$ represents a hydrogen or a protective group of carboxylic acid, Hal represents a halogen atom, and the hydrogens at the 6- and 7-positions have cis configuration, the pharmaceutically acceptable salts thereof and processes for producing the same.

The compounds represented by the general formula (I), (II), ..... may be named Compound [I], Compound [II], ....., respectively.

UNITED STATES PATENT AND TRADEMARK OFFICE
CERTIFICATE OF CORRECTION

PATENT NO. : 4,734,494
DATED : March 29, 1988
INVENTOR(S) : TADASHI HIRATA, ET AL.

Page 2 of 2

It is certified that error appears in the above-identified patent and that said Letters Patent is hereby corrected as shown below:

Heretofore, a carbacephem compound, which is named according to the nomenclature in J. Am. Chem. Soc. *96*. 7584 (1974), wherein the sulfur atom of cephalosporin in substituted with a carbon atom and which has a substituted methyl group at the 3-position is described in the above reference and J. Med. Chem. *20*, 551 (1977). However, no compound of this type having especially strong antibacterial activity has been reported.--

Column 7, line 4, "[4,2,0]cis-2" should read
--[4,2,0]oct-2--.

Column 8, line 7, "added" should read --adjusted--.

Column 10, line 59, "2en" should read --2-en--.

Signed and Sealed this

Nineteenth Day of July, 1988

Attest:

DONALD J. QUIGG

Attesting Officer

Commissioner of Patents and Trademarks